United States Patent [19]

Hodgen

[11] Patent Number: 5,219,729
[45] Date of Patent: Jun. 15, 1993

[54] FERTILITY ASSAY
[75] Inventor: Gary D. Hodgen, Norfolk, Va.
[73] Assignee: Serono Laboratories, Inc., Mass.
[21] Appl. No.: 160,165
[22] Filed: Feb. 25, 1988
[51] Int. Cl.$^5$ .............. G01N 33/567; G01N 33/566; G01N 33/53; C12Q 1/02; C12Q 1/00
[52] U.S. Cl. ............................... 435/7.21; 436/501; 436/510; 436/814; 436/503; 435/29
[58] Field of Search ............. 436/503, 501, 510, 814; 435/29, 7.21

[56] References Cited

U.S. PATENT DOCUMENTS

3,992,520 11/1976 Gwatkin .............................. 424/561

OTHER PUBLICATIONS

Kamada et al (1985) Blocking of human fertalization in vitro . . . Am J Obst Gyn 153(3) 328–331.
Krumins et al (1981) High Affinity binding of lower density . . . Biochem J 196:481–488.
Wassarman (1988) Zona Pellucida glycoprotein Am Rev Biochem 57:415–42.
"Penetration of Human Spermatozoa into the Human Zona Pellucida and the Zona-Free Hamster Egg: A Study of Fertile Donors and Infertile Patients" by James W. Overstreet, et al., The American Fertility Society (1979), pp. 534–542, vol. 33, No. 5.
"Penetration of the Zona Pellucida of Nonliving Human Oocytes By Human Spermatozoa In Vitro" by James W. Overstreet et al., Fertility and Sterility, Jul. 1976, pp. 815–831, vol. 27, No. 7.
"Hemi-Zona Pellucida for Assessing Human Sperm Funtion" by C. C. Coddington, L. J. Burkman, G. D. Hodgen, Fifth World Congress on In Vitro Fertilization And Embryo Transfer, Program Supplement Apr. 5–10, 1987, Abstract PP-91, p. 60.
"Hemi-Zona Assay (HZA): Is Human Sperm Binding To The Zona Pellucida Predictive Of In Vitro Fertilizing Potential?" by L. J. Burkman, C. C. Coddington, T. F. Kruger, G. D. Hodgen, 43rd Annual Meeting Of The American Fertility Society, Program Supplement, Abstract 212, Reno 1987.
"The Kinetics of Human Sperm Binding to the Human Zona Pellucida and Zona-Free Hamster Oocyte In Vitro" by Sherry L. Singer et al., Gamete Research (1985), vol. 12, pp. 29–39.
"Sperm Binding Activity of the Zona Pellucida of Immature Mouse Oocytes" by Nicholas L. Cross et al., Cell Biology International Reports, vol. 10, No. 7, Jul. 1986, pp. 545–554.
"Hemizona assay: assessment of sperm dysfunction and prediction of in vitro fertilization outcome*", Fertility and Sterility, vol. 51, No. 4, Apr. 1989, pp. 665–670.
"Validation of the hemizona assay in a monkey model: influence of oocyte maturational stages*" by Sergio Oehninger et al., Fertility and Sterility, vol. 51, No. 5, May 1989. pp. 881–885.
"Functional Aspects Of Human Sperm Binding in the Zona Pellucida Using the Hemizona Assay" by C. C. Coddington et al., pp. 1–28 (Confidential Submitted Journal of Andrology).
"Antagonistic and agonistic properties of saccharide moieties in the hemizona assay" by Sergio Oehninger et al., Fertility and Sterility, vol. 53, No. 9, Jan. 1990, pp. 001–007.
"Research on Spermatozoa in Assisted Reproduction—Chapter 13" (Part One and Part Two) by Susan E. Lanzendorf et al., pp. 341–371.
Running Title: "Teratozoospermia and zona pellucida binding" by D. R. Franken (Confidential and In Preparation) pp. 1–21.
"Clinical Assessment of Fertility Potential for Vasectomy Reversal Patients: Hemizona Assay (HZA)" by C. C. Coddington et al., pp. 1–15 (Confidential—In Preparation).
Running Title: "Hemizona Assay and T-6 Antibody" by C. C. Coddington et al., pp. 1–20 (Confidential—In Preparation).
"Assisted Reproductive Technologies May Obviate Apparent Immunologic Infertility" by D. Franken, pp. 1–17 (Submitted Int'l Journal of Fertility—Confidential).
Burkman, et al "The hemizona assay (HZA): development of a diagnostic test for the binding of human spermatozoa to the human hemzona pellucida to predict fertilization potential" Fertil Steril 49:688, 1988. (1st reference in Oehninger, et al. Fertil. Steril. 51:665, 1989. Coddington, et al. 5th World Congress on In Vitro Fertilization and Embryo Transfer, Program Supplment Apr. 5–10, 1987 Abstract p. 91 p. 60.
Burkman et al 43rd Annual Meeting of the American Fertility Society, Program Supplement, Abstract 212, Reno 1987.

*Primary Examiner*—Christine M. Nucker
*Assistant Examiner*—D. R. Preston
*Attorney, Agent, or Firm*—Ostrolenk, Faber, Gerb & Soffen

[57] ABSTRACT

A new diagnostic assay of sperm function has been found for infertility treatment and monitoring programs. The hemizona assay (HZA) measures tight binding of human spermatozoa to the human hemizona pellucida.

18 Claims, No Drawings

FERTILITY ASSAY

BACKGROUND

It has been estimated that male reproductive dysfunction is the primary factor in up to 40% of infertile couples. This high incidence of male factor infertility has promoted an intense search for reliable means to predict human sperm fertilizing potential in vivo and in vitro. For ethical reasons, scientists and physicians have frequently hesitated to perform direct diagnostic functional assessments; that is, binding of human spermatozoa to intact viable human oocytes has usually been regarded as an inappropriate test system. However, reliable and discriminating prognostic assays are needed to determine which infertile men are likely to achieve fertilization in vitro or impregnate their wives when assisted by artificial insemination (AIH).

Tight of human spermatozoa binding to the human zona pellucida represents the first critical event in gamete interaction leading to fertilization and activation of development. This binding step may provide unique information predictive of ultimate sperm fertilizing potential. Due to species specificity, human spermatozoa will bind firmly to only human zonae pellucida. Overstreet J W, Hembree W C: Penetration of the zona pellucida of nonliving human oocytes by human spermatozoa in vitro. Fertil Steril 27:815, 1976.

THE INVENTION

Applicants have discovered a new diagnostic assay for tight sperm binding to the mammalian hemizona pellucidae. This test is preferred for use with humans, but is usable for other mammals, i.e., cows, pigs, simean primates (e.g., Rhesus monkeys), horses, etc. In a preferred embodiment a mammalian oocyte is cut in half using a micromanipulation knife. Each of the two matched zona hemispheres provides a test reagent having advantages: 1) the two halves (hemizonae) created are functionally (qualitatively) equal zona surfaces, allowing a controlled comparison of binding; 2) the very limited number of recovered human oocytes is amplified since an internally controlled test can be carried out on a single oocyte; and 3) ethical objections to possible inadvertent fertilization of a viable oocyte are eliminated by first cutting the egg into halves.

Our findings are reported in three segments. In Part I, we examined the feasibility of sperm binding to these hemizonae. For Part II, attention was given to elucidating the kinetics of tight sperm binding and then to optimizing measurement of sperm binding to hemizonae. Finally, in Part III, we performed initial tests using the hemizonae assay (HZA) to distinguish functional differences between the sperm from known fertile men versus men whose sperm had failed to fertilize their wives' oocytes in one or more in vitro fertilization (IVF) treatment cycles. In these latter cases, male infertility was believed to be the limiting factor in achieving fertilization.

DESCRIPTION OF THE INVENTION

Oocytes

Sperm-hemizona reactions are known to be species specific. The procedures described here are with appropriate modifications, applicable to the preparation of comparable reagents from the ovarian tissue of various mammals, as well as humans.

Oocytes were obtained from two sources: 1) ovarian tissue that was collected postmortem, and 2) donated unfertilized oocytes from the IVF treatment program. In the first instance, the ovarian tissue was excised within 24 hours of death and stored at +4 C. in phosphate buffered saline (PBS;Gibco, New York). Between 2 to 48 hours later, manual dissection was carried out following the protocol of Overstreet. See Overstreet J W, Yanagimachi R, Katz D F, Hayashi K, Hanson F W: Penetration of human spermatozoa into the human zona pellucida and the zona-free hamster egg: a study of fertile donors and infertile patients. Fertil Steril 33:5, 1980. After careful mincing of the tissue, zona-intact oocytes denuded of granulosa cells were recovered and placed directly into a 2M solution of dimethyl sulfoxide (DMSO) in PBS. One to four oocytes were transferred with 30 ul of DMSO solution to the interior of glass microcapillary tubes (100 ul volume; Corning, N.Y.). The tube ends were sealed with Critoseal (Fisher Scientific, Springfield, N.J.), and immediately frozen at −70 degrees C. The oocytes were either thawed in a three-step or a one-step process, with no apparent difference on later zona function. The thawed oocytes were rinsed several times in PBS, and cut by micromanipulation into nearly equal halves yielding the matched hemizona. A smaller number of immature or postmature oocytes was donated by IVF patents. Such oocytes had been collected by follicular aspiration following ovarian stimulation using exogenous gonadotropin for IVF therapy using the method of Rosenwaks Z, Muasher S J: Recruitment of fertilizable eggs. In In Vitro Fertilization Norfolk, Edited by H W Jones, Jr, G S Jones, G D Hodgen, Z. Rosenwaks. Baltimore, Williams and Wilkins, 1986, p 30. About half of these eggs were frozen in the DMSO solution on the same day they became available (24 to 48 hours after aspiration); the remaining eggs were stored up to 72 hours under oil (+4 C.) until they were cut by micromanipulation and then immediately used in sperm binding tests. Again, these differences in handling had no discernible effect on hemizona performance in tight sperm binding.

Oocytes which have been previously collected can be stored and handled as described below.

STORAGE AND HANDLING OF OOCYTES

Oocytes with intact zonae pellucida were obtained from the Embryology laboratory of the Norfolk IVF program. These oocytes donated for the study were nonfertilizable and arrested at Prophase 1 of maturation after 24 hours of culture. Such oocytes had been collected by follicular aspiration following ovarian stimulation using exogenous gonadotropin for IVF therapy (Rosenwaks and Muasher 1986). Pairs of oocytes were placed in small plastic vials each containing 0.5 ml of 1.5M magnesium chloride (Mallinckrodt Chemical Works, St. Louis, Mo.) with 0.1% Polyvinylpyrrolidone (PVP, MW 36000, Sigma Chem Co., St. Louis, Mo.). All salt treated oocytes were stored at room temperature.

The control oocytes were collected from surgically excised ovarian tissue, using the protocol of Overstreet and Hembree (1976). Zona intact oocytes were denuded of granulosa cells and placed directly into a 2.0M solution of DMSO in phosphate buffered saline. The buffered saline solution employed had a pH of about 7.4 to about 7.2. The salt, i.e., NaCl, concentration can range from about 0.90 to about 0.92 wt. %.

Media other than DMSO can be used. They include glycerol, saline and the like. Mixtures are operable. The oocytes were transferred in pairs to the standard plastic straws used in cryopreservation laboratories; straw ends were plugged and frozen in a single step at −70 degrees C.

On the day prior to each assay, the desired number of oocytes was removed from salt storage. As needed for controls, additional oocytes frozen in DMSO solution were thawed in a single step and removed from the straws. Each oocyte was washed (5×) in Hams F10 (Gibco Co., New York, N.Y.), plus 7.5% of heat inactivated, human fetal cord serum. These DMSO oocytes were used to produce control hemizonae during testing.

A complete Narishige micromanipulation system (Narishige, Tokyo, Japan) was used during the cutting procedures of the oocytes. (Burkman et al 1988). A number 11 microscapel blade was glued to the side of a metal holding bar (12 cm long; 3 mm diameter); the bar was attached to one micromanipulator. A 100 mm plastic petri dish (Falcon #25382) served as the cutting chamber and was filled to a depth of 3 to 4 mm with culture medium (Ham's F10). The cutting blade was positioned and used to cut a swallow groove into the bottom of the plastic dish. One egg was transferred to the working area of the dish using a glass micropipette; the egg was centered on the cutting groove. Using a total magnification of 200×, the blade was lowered slowly, first partially flattening the egg then finally initiating a midline cut into the zona. Further lowering of the blade produced two cleanly cut hemizonae. The ooplasm inside was then dislodged by vigorous pipetting. Each hemizona pair was placed in a separate 50 ul droplet of medium in a petri dish, covered with mineral oil (Fishcher Scientific, Fair Lawn, N.J.) and stored overnight at +4 degrees C. Previous experiments showed that bisecting of the zona by surgical micromanipulation produced only small deviations from an exact 50/50 cut (Burkman et al 1988).

Oocytes and hemizona can also be stored using dimethysulfoxide storage, culture storage (up to 24 hours) and/or freezing techniques.

Cutting oocytes into hemizona (HZ) by micromanipulation

A complete micromanipulation apparatus equipped with suction (positioning) and cutting implements (Narishige, Tokyo, Japan) was utilized for bisecting the eggs. An inverted, phase contrast microscope (Nikon Diaphot, Garden City, N.Y.) was equipped with a pair of Narishige micromanipulators connected to pipettes, knives and aspiration tools, operating with working "arms" for using same, (i.e., model MO 102); the connecting tubing was filled with mineral oil. A micropipet puller (model PP83 made by Narishige, Tokyo) was used for initial preparation of the egg-holding pipet from thin-walled capillary tubing (inner diameter=0.6 mm; outer diameter=0.9 mm; Drummond Scientific, Broomall, Pa.). The pipet tips were fire-polished and partially closed using a Narishige microforge (model MF-79). When completed, the outer diameter of the tip was approximately 100 um; the residual opening measured 15-20 um in diameter. The pipet was then heated and bent in two places so that the tip was oriented perpendicularly to the cutting blade. A #11 microscalpel blade was glued to the side of a metal bar (12 cm long; 3 mm diameter). The bar was bent to give a sigmoidal shape; the tip of the bar had a flat, vertical face for attachment of the blade.

A 100-mm plastic petri dish (Falcon #25382) served as the cutting chamber. Culture medium (Ham's F-10; Gibco, New York) or PBS was poured into the dish, to a depth of 3 to 4 mm. After the egg holding pipet and the cutting blade were positioned at the center and bottom of the dish, the egg was transferred to the working area of the dish using a finely drawn glass pipet. The egg was held at the tip of the holding pipet by gentle suction while the blade was centered over the egg. Using a total magnification of 200×, the blade was lowered slowly, first partially flattening the egg then finally initiating a midline cut into the zona. A further lowering of the blade, along with 1 to 2 side-to-side excursions, produced two cleanly cut hemizonae. Repeated practice using frozen-thawed mouse oocytes proved useful in honing the technique.

An alternative method of cutting the oocytes into halves involves making a groove in the surface which holds the zona, placing the oocyte on the groove so that equal portions are on both sides of the groove, and gently lowering the cutting blade onto the oocyte to cut it into equal parts.

The dense ooplasm inside each hemizona was then dislodged by vigorous pipetting. Only one egg was cut at a time to assure that matched hemizonae remained paired for subsequent sperm binding tests. Each hemizonae pair was placed in a separate 50 ul droplet of medium in a petri dish, covered with mineral oil and stored at about 2-6 degrees C., preferably at about 4 degrees C.

The reliability of the "halving" process is usually about ±3%. Most halving procedures yield hemozonae having 47/53 to 50/50 percentage ratios of active sites with about 3,000 to about 5,000 active binding sites per half. Given the high number of binding sites, the halves are virtually always functionally identical halves.

Semen Sources

The basic semen parameters (sperm concentration and percentage of motile cells) were usually assessed with a computerized videoanalysis system (CASA, Cryo Resources, Ltd, New York). Otherwise, the sperm concentration was calculated using a hemocytometer with Neubauer ruling and percentage motility was assessed by scoring 100 sperm per slide. The "Bright-line" counting chamber (02-671-5) and hemacytometer set (02-672-5) of Fisher Scientific Instruments are suitable.

In general, any suitable source of semen can be employed in carrying out the invention. The Examples given below illustrate some sources of useful semen.

EXAMPLES

Examples 1-4 utilized discarded portions of semen from men undergoing semen analysis. Semen aliquots were used only when sperm motility exceeded 40% and sperm concentration was $\geq 40 \times 10^4$/ml. For these men, fertility status was unknown. For the kinetics experiments in Examples 5 and 6, the semen donors had all fathered a child during the preceding 24 months. For Example 7, semen was obtained from husbands who had not achieved fertilization of their wives' oocytes on one or more occasions of IVF treatment within the preceding 12 months. Seminal sperm concentrations exceeded $28 \times 10^6$ for all specimens used in Example 7.

Sperm was prepared for the examples via the following procedure: An aliquote of semen (0.5 ml) was diluted with 1 ml of Ham's F-10 culture medium, supplemented with 7.5% heat-inactivated, human fetal cord serum. After centrifugation (5 min×33 g), the pelleted sperm were washed a second time. The second pellet was overlayed with 0.5 ml of F10 medium and incubated (37 C., 5% $CO_2$ in air) to effect a "swim-up" separation. See McDowell J S: Preparation of spermatozoa for insemination in vitro. In In Vitro Fertilization Norfol, Edited by H W Jones, Jr, G S Jones, G D Hodgen, Z Rosenwaks. Baltimore, Williams and Wilkins, 1986, p 162. After 1 to 2 hours of incubation, the sperm supernatant was recovered and utilized for hemizona binding testings.

EXAMPLE 1

Determining the precision of zona cutting

Accuracy in producing matched hemizonae of nearly equal size was assessed for 12 cut oocytes. The concave depth of each cup-shaped hemizona was measured with a reticle and the data were compared within each hemizona pair.

Bisecting of the zona by surgical micromanipulation showed small deviations from an exact 50/50 cut. When the sizes of matching hemizona halves were compared, the mean difference in the depth of the concave hemizona shells was 10±2.0% (median difference=8.1%). Interestingly, individual unmatched hemizona varied between 70 and 105 um in depth, reflecting the unequal sizes of respective intact oocytes before they were cut.

EXAMPLE 2

Comparing sperm binding of thawed postmortem oocytes versus never-frozen oocytes discarded from the IVF laboratory Six experiments were carried out using sperm from different donors; a total of 13 intact eggs was studied. A portion of the swim-up supernatant was diluted with F10 medium to give a motile sperm concentration of 100,000/ml. Two sperm drops (50 ul volume) were placed under oil; 1 intact oocyte from postmortem tissue was added to the first drop, while an intact oocyte from IVF treatment was placed in the matching drop. The duration of coincubation at 37 degrees C. was 2 to 3 hours. The number of sperm tightly attached to the zona pellucida was counted after vigorous pipetting (5×) using a narrow bore pipet and fresh medium.

The use of oocytes from postmortem tissue versus eggs discarded from IVF did not significantly influence sperm binding potential of the zona pellucida. After vigorous pipetting, the number (X±SEM) of firmly bound spermatozoa was not statistically different from the intact postmortem zona (5.0±1.9, n=6) versus the intact IVF zona (5.4±2.1, n=7).

EXAMPLE 3

Measuring the sperm binding properties of the zona with and without cutting via micromanipulation We wished to test whether potential release of ooplasmic debris during the cutting process would alter sperm binding. In 5 experiments, a 50 ul droplet of swim-up sperm was placed under oil (250,000 motile/ml). For each experiment, 1 to 2 intact zonae and 2 to 3 hemizona pairs were placed in the sperm droplet. After 2 to 3 hours of coincubation, the number of tightly bound sperm on the zona surface was assessed. The total number of spermatozoa associated with the outer zona surface was first counted within the insemination droplet, before disturbing intact eggs or hemizonae (sperm with loose association or tight binding were included). This approach was used since it was not known whether the spherical intact egg versus the hemizona shell could be pipetted with the same shear force to remove loose sperm. A single pipet in each experiment was then used to vigorously rinse each intact egg and hemizona five times, after which the sperm counts were repeated. The number of sperm associated with the inner surface of the hemizona was likewise counted after rinsing. For statistical comparisons between intact zona and hemizona, the number of hemizona attachments was, of course, doubled in each experiment.

When assessed before pipetting, total sperm association (loose and tight attachments) with the outer surface of cut hemizonae was not different from that observed for the intact zonae. When the total number of associated spermatozoa was doubled for all hemizonae, the means were not statistically different: hemizonae (57±16, n=12) versus the intact egg (64±21, n=8). After the pipetting step for removing loosely associated sperm, the number of tightly attached sperm was 11.1±3.6 (X±SEM) for the intact egg versus 20.9±8.1 for the hemizona (p>0.05). Some tight sperm attachment did occur on the inner zona surface of the hemizona. Following the rinsing step, the mean number attached to the outer surfaces was 10.4±5.1 (X±SEM) compared to 1.6±0.8 on the inner surface n=8).

EXAMPLE 4

Determining whether matching hemizonae have equal potential for sperm binding For these experiments, each test dish had 2 matching sperm drops (100,000 motile sperm/ml). One hemizona was added to the first drop and the matching HZ was placed in the second drop. Eight matched pairs were tested, using sperm of 5 different men. Coincubation lasted 2 to 3 hours, after which sperm attachment was assessed for the outer zona surface as described above in Example 3.

Visual counting (i.e., direct observation) is the preferred method of quantifying attachments. However, the number of sperm bound can also be determined via the use of chemical/biological parameters which indicate sperm viability. Thus, one can measure the amount of DNA in a sperm sample by measuring the level of acrosome or other unique proteinaceous component(s) of sperm. In addition, the degree of flagellar motion can also be measured as an indicator of viability. Various procedures using these and/or other techniques can be employed.

Matching hemizonae showed no detectable difference in their capacity for tight sperm binding to the outer zona surface. When the hemizona with the larger number of bound sperm were assigned to group 1, and the matching HZ assigned to group 2, there was no statistically significant difference between the group means (3.5±0.6 and 2.6±0.4, n=8).

EXAMPLE 5

Optimizing the kinetics of sperm binding to hemizonae

The sperm of four known fertile men were coincubated with hemizonae for periods up to 8.5 hours. See Burkman L J: Temporal pattern of hyperactivation-like motility in human spermatozoa. Biol of Reprod, Supplement (1) 34:226, 1986. Seminal aliquots were washed twice with Ham's F-10 medium containing serum and prepared for a swim-up incubation. The recovered spermatozoa were diluted to give a final motile concentration of 500,000/ml. At least 10 sperm drops (2 to 3 drops per time interval) were prepared and covered with oil before adding the hemizonae.

A minimum of five matched pairs of hemizonae were utilized per experiment. Two hemizonae were analyzed per time interval constituting duplicate tests. The hemizonae were assigned so that matching pairs were utilized at different times. This aspect of the protocol permitted comparison of sperm attachment over time for the same egg.

All hemizonae began coincubation at the same time. After periods of 1, 2.5, 4.0, 5.5 and 8.5 hours, the hemizonae were removed to assess sperm attachment. They were pipetted five times to dislodge loosely associated sperm, and the number of tightly bound sperm on the outer surface was counted. Care was taken to identify matching HZ for later statistical evaluation.

The spermatozoa from four known fertile men showed similar trends for binding to the hemizonae over the 8.5 hour period. The kinetic curves for two representative experiments, illustrate a high and a low binding pattern. Uniformly, tightly bound sperm were present on the hemizona surface within one hour of coincubation. Here, the number ($X \pm SEM$) of bound sperm was $39.1 \pm 12$ (4 men, 9 hemizona pairs). In this study, maximal binding occurred at 3.5 hours for one man, 4.0 hours for two others, and at 5.5 hours for the fourth donor. Interestingly, there was a consistent decline in the number of sperm tightly attached to the hemizonae at the first observation time beyond the binding peak. Thereafter, the numbers for tightly bound sperm remained almost constant through 8.5 hours.

The change in sperm binding over time between matching hemizonae was also assessed in this first kinetics study. Paired data were analyzed for three coincubation intervals (1 vs 4 hours, 2.5 vs 5.5 hours, and 4 vs 8.5 hours, with 4 to 6 hemizona pairs per interval). During the 1 vs 4 hour interval, all binding slopes rose dramatically. The overall increase was $17.5 \pm 4.4$ sperm/hour ($X \pm SEM$). Between 2.5 vs. 5.5 hours, the rise was not sustained; in most instances, the slopes were shallow, coinciding with peak binding during this period (range: $-8$ to $+13.0$ sperm/hour). Uniformly, relative sperm binding to matched hemizonae declined between 4 and 8.5 hours ($-10.6 \pm 4.8$ sperm/hour; $X \pm SEM$).

EXPERIMENT 6

Characterization of the sperm binding pattern during the first four hours of coincubation The data from experiment 5 indicated the need for more detailed information on the early coincubation period, specifically the 1 to 4 hour interval. Semen specimens were received from five different fertile donors (four of these had been used in experiment 5). The swim-up supernatants were obtained as usual. For each experiment, one sperm droplet was prepared under oil (500,000 motile sperm/ml) and the two matching hemizonae were added. Coincubation was briefly interrupted at the end of 1, 2, 3, 4 and 5.5 hours, with a final reading on tightly bound sperm numbers at 8.5 hours. At these times, the two hemizonae were quickly recovered and placed in a warm droplet of rinsing medium (Ham's F-10) under oil. The sperm dish was immediately returned to the incubator. Hemizonae were rinsed five times to dislodge loosely associated spermatozoa. While counting, the microscopic stage area was warmed (35 degrees to 37 degrees C.) using a stream of air (Arenberg Sage Air Curtain Incubator, model 279, Jamaica Plain, Mass.). For each hemizona, the number of sperm bound to the outer surface was counted. The matched pair was then transferred back to the original sperm drop for further coincubation. The counting procedure was carried out during the final 8 to 10 minutes of each assessment interval.

Representative sperm binding curves from three of six experiments were prepared. In all six experiments, the means for the matched pairs of hemizonae revealed that a consistent peak in sperm binding was reached within approximately four hours of coincubation after which there was a slight decline through 8.5 hours. Importantly, by the use of frequent counts, our observations typically revealed a nearly linear increase in tight sperm binding between one and four hours.

Reproducibility of binding for matched hemizonae was high. In five of the six cases, differences between paired hemizonae ranged from 8 to 20% for the number of sperm bound at 4 hours. The paired curves usually showed remarkable consistency in the slope of the rising sperm binding phase.

The data were then pooled across all six experiments and the mean number of sperm bound at each hour identified. The calculated 95% confidence interval (two-tailed test, $df=11$) for the 4 hour data was 60.3 to 128.5 tightly bound sperm; these values compare well with the matching 4 hour confidence interval from our first kinetics study (75.4 to 122.5; experiment 5a).

EXAMPLE 7

Determining whether sperm binding to the hemizona is correlated with sperm fertilizing ability Ten experiments were performed comparing the hemizona binding capacity for the sperm of eight known fertile men versus eight husbands who had not achieved fertilization of their wives' eggs during one or more IVF treatments. The semen from all of these men had a sperm concentration exceeding $28 \times 10^6$/ml. Eleven had a percentage motility $>37\%$; five of the unsuccessful IVF patients had motility $\leq 37\%$. Semen aliquots were washed with the standard F-10 medium. After a one hour swim-up, supernatant spermatozoa were diluted with F-10 medium, and sperm drops were prepared under oil (250,000 motile sperm/ml). In each experiment, one half of the hemizona pair was placed with the sperm from a fertile man, while the matching hemizona was coincubated with sperm from a previously unsuccessful IVF husband. In two instances, duplicate experiments were performed for the known fertile and infertile men. The hemizonae were removed after 3 to 4 hours of coincubation, rinsed (as above), and the number of sperm tightly bound to the outer surface was counted. For each experiment, the ratio of sperm bound was then calculated (infertile number/fertile number).

EXAMPLE 8

Using matched hemizona pairs in all ten experiments, the spermatoza from known fertile men bound to the hemizona more efficiently than sperm from IVF husbands who had not achieved fertilization of their wives' egg in vitro. For this limited patient group, objective comparisons of the matching hemizona data were made possible by calculating the ratio for the HZA Index of tightly bound sperm (See the Table).

$$HZA \text{ Index}: \frac{\text{number of infertile sperm bound}}{\text{number of fertile sperm bound}} \times 100$$

For these 10 experiments, the mean value for the HZA Index was 21±8 (X±SEM). Here, 95% of the values were less than 62. Therefore, an HZA Index of 62 may represent a preliminary threshold, such that lower HZA indices may be prognostic of very low to nil fertilizing potential. The overall number (X±SEM) of sperm bound was significantly different for the two groups tested (34.0±8.1 fertile versus 5.9±2.3 infertile, p<0.01).

Examples 1-7 demonstrate the feasibility of the HZA as a tool in predicting the fertilizing potential of human spermatozoa. See Coddington C C, Burkman L J, Hodgen G D: Hemizona pellucida for assessing human sperm function. The Fifth World Congress on IVF/ET Norfolk, Va., Apr. 5-10, 1987. The American Fertility Society, Program Supplement p 60 (abstract). Having examined the kinetics of sperm binding to the hemizona, applicants then demonstrated that sperm from known fertile men exhibited a significantly (p<0.05) higher HZA Index than sperm from men seeking infertility treatment by IVF. See Burkman L J, Coddington C C, Kruger T F, Rosenwaks Z, Hodgen G D: Hemizona assay (HZA): Is human sperm binding to the zona pellucida predictive of in vitro fertilizing potential? 43rd Annual Meeting of The American Fertility Society, Reno, Nev., September, 1987 (abstract).

In initial studies, it was found that accurate bisecting of the human zona pellucida was not difficult. Hence, differences in the numbers of sperm bound to matching hemizona were not due to dissimilar surface areas. Most probably, the large number of potential sperm binding sites on the zona surface makes the small differences in hemizona size insignificant. Secondly, it is noteworthy that there were no obvious differences in sperm binding capacity of postmortem oocytes versus extra IVF oocytes matured in vitro. A similar finding has been reported by Cross. See Cross N L, Lambert H, Samuels S: Sperm binding activity of the zona pellucida of immature mouse oocytes: Cell Biol Internat 10:545, 1986. In that study, no differences were detected in tight binding of mouse spermatozoa to the mouse zonae pellucida of immature follicular oocytes versus ovulated oocytes.

In the third example, it was clear that extrusion of the ooplasm during the cutting process did not adversely affect the HZA coating the hemizona surface with interfering substances. The observation of limited right sperm binding on the inner surface of the zona was not surprising. Other investigators have identified sperm-binding components on the inner surface of hamster zonae pellucida, although at concentrations well below that detected on the outer zona surface.

The results from Example 4 gave crucial evidence that establishing an assay using hemizona pairs was statistically warranted, as would be required for a reliable assay. Here, the matching hemizona halves showed equivalent capacities for sperm binding, thus confirming our proposed use of the matched hemizona halves as an internal control against the known variable sperm binding capacities of different eggs.

The hourly observations made in Examples 5 and 6 demonstrated the nearly linear increase in sperm binding to hemizonae through 4 hours of coincubation. These results confirmed that coincubation times of about one to about six are useful, with maximal sperm binding to the hemizona in HZA achieved after approximately 4 hours. Times of about 4 to 5 hours are preferred.

Our data emphasize that aged sperm (≧7 hours of capacitation), having diminished capacity to bind tightly to the zona pellucida, may not be suitable for HZA evaluation. Similarly, we anticipate that some eggs will have such poor binding characteristics, as to have no discriminating power for testing of sperm binding. See also Singer S L, Lambert H, Overstreet J W, Hanson F W, Yanagimachi R: The kinetics of human sperm binding to the human zona pellucida and zona-free hamster oocyte in vitro. Gamet Res 12:29, 1985.

Our early experience with the HZA has suggested a model to describe fertilizing potential in relationship to the HZA Index. Most men having normal fertility will fall into the population with an HZA Index approaching or exceeding 100. A second population of truly infertile men is represented where the HZA Index will be low or equal to zero. The intermediate region represents those men with impaired fertility of varying degrees.

TABLE

Comparison of number of sperm tightly bound to pairs of matched hemizona for proven fertile men versus infertile men after 4 hours of coincubation.

| Experiment # | NUMBER OF TIGHTLY BOUND SPERM | | HZA INDEX |
|---|---|---|---|
| | Infertile Men | Fertile Men | Infertile/Fertile × 100 |
| 1 | 20 | 64 | 31 |
| 2 | 10 | 10 | 63 |
| 3 | 0 | 10 | 0 |
| 4 | 17 | 28 | 61 |
| 5 | 0 | 17 | 0 |
| 6 | 3 | 35 | 9 |
| 7 | 2 | 44 | 5 |
| 8 | 0 | 90 | 0 |
| 9 | 4 | 15 | 27 |
| 10 | 3 | 21 | 14 |

Cutting of zona into more than two pieces

While the specification speaks mainly of hemizona (i.e., halves of zonae), it should be remembered that other fragments, quarters, sixths, eighths, etc. are also operable in the invention. In fact, in view of the cut zona's residual activity, it is likely that any functionally equivalent pieces of zonae can be used without significantly affecting reactivity.

Thus, given only the physical constraints necessitated by the size of mammalian oocytes, the number of equal segments into which zonae can be cut can range from about 2 to about 8. It is highly preferred that at least two functionally equal fragments be employed in each assay.

Reasonable variations, such as those which would occur to a skilled artisan, can be made herein without departing from the scope of the invention.

We claim:

1. A diagnostic assay for predicting sperm fertilizing potential which comprises providing 2 to 8 fragments of mammalian zona pellucida of the same oocyte, contacting a first portion of the fragments with the sperm from the same species to be assayed under binding conditions, contacting a second portion of the fragments with sperm from the same species of known fertilizing potential under binding conditions, said first and second portions having functionally equivalent sperm binding activity, and comparing the resulting sperm binding to one portion with the sperm binding to the other portion.

2. The assay of claim 1 wherein the zona pellucida fragments employed are obtained from human ovarian tissue.

3. The assay of claim 2 wherein each zona pellucida fragment is a hemizona.

4. The assay of claim 1 wherein each zona pellucida portion is a hemizona.

5. The assay of claim 4 in which the sperm and hemizona are human.

6. The assay of claim 5 in which sperm which is not firmly bound is separated from the portions after the contacting of the portions with the sperm and before the comparison step.

7. The assay of claim 6 in which the hemizona are co-incubated.

8. The assay of claim 7 in which the hemizona are provided by disecting the oocyte.

9. The assay of claim 1 in which the fragments are provided by disecting the oocyte.

10. A diagnostic assay for predicting sperm fertilizing potential which comprises contacting sperm to be assayed under binding conditions with a first portion of mammalian zona pellucida of an oocyte from the same species, contacting sperm from the same species of known fertilizing potential under binding conditions with a second separate portion of mammalian zona pellucida of the same oocyte, said first and second portions having functionally equivalent sperm binding activity, and comparing the resulting sperm binding to one portion with the sperm binding to the other portion.

11. A test kit for predicting sperm fertilizing potential comprising 2 to 8 separate containers each of the containers containing a one-half to one-eighth fragment of mammalian zona pellucida of the same oocyte, each of the containers containing functionally equivalent sperm binding activity.

12. The test kit of claim 11 wherein the zona pellucida fragments are hemizona.

13. The test kit of claim 12 wherein the hemizona pellucida are human.

14. The test kit of claim 11 in which the zona pellucida fragments are human.

15. The test kit of claim 14 wherein the zona pellucida fragments are hemizona.

16. The test kit of claim 15 in which each container contains a salt solution and the hemizona.

17. The test kit of claim 11 in which each container contains a salt solution and zona pellucida fragment.

18. A test kit for predicting sperm fertilizing potential comprising separate containers each of which contain a different portion of mammalian zona pellucida of the same oocyte, each of the portions having functionally equivalent sperm binding activity.

* * * * *